United States Patent
Patel et al.

(10) Patent No.: US 8,454,623 B2
(45) Date of Patent: Jun. 4, 2013

(54) INSTRUMENT FOR INSERTION AND DEPLOYMENT OF FEATURES ON AN IMPLANT

(75) Inventors: Nirali Patel, Carlsbad, CA (US); Yang Cheng, Foothill Ranch, CA (US); Budi Budikentjana, San Diego, CA (US)

(73) Assignee: Alphatec Spine, Inc, Carlsbad, CA (US)

( * ) Notice: Subject to any disclaimer, the term of this patent is extended or adjusted under 35 U.S.C. 154(b) by 238 days.

(21) Appl. No.: 12/944,507

(22) Filed: Nov. 11, 2010

(65) Prior Publication Data

US 2011/0112587 A1 May 12, 2011

Related U.S. Application Data

(60) Provisional application No. 61/260,323, filed on Nov. 11, 2009.

(51) Int. Cl.
*A61B 17/56* (2006.01)

(52) U.S. Cl.
USPC .......................................... 606/99; 623/17.11

(58) Field of Classification Search
USPC ................. 606/99; 623/17.11, 17.16; 81/56, 81/57, 461
See application file for complete search history.

(56) References Cited

U.S. PATENT DOCUMENTS

| | | | | |
|---|---|---|---|---|
| 2,479,225 | A | * | 8/1949 | Gann ................................ 81/56 |
| 5,938,701 | A | * | 8/1999 | Hiernard et al. ................ 606/99 |
| 6,258,090 | B1 | | 7/2001 | Jackson |
| 6,833,066 | B2 | | 12/2004 | Baumann et al. |
| 6,953,477 | B2 | | 10/2005 | Berry |
| 7,481,813 | B1 | | 1/2009 | Purcell |
| 7,559,930 | B2 | | 7/2009 | Allard et al. |
| 2006/0293748 | A1 | * | 12/2006 | Alexander et al. ......... 623/17.11 |
| 2008/0221586 | A1 | | 9/2008 | Garcia-Bengochea et al. |

* cited by examiner

*Primary Examiner* — Kevin T Truong
*Assistant Examiner* — Christian Sevilla
(74) *Attorney, Agent, or Firm* — Michael J. Loi (57) ABSTRACT

A surgical instrument for inserting an implant includes a first shaft having an axial bore and including a distal end configured to actuate a first feature of a spinal implant and a second shaft extending through the axial bore of the first shaft and including a distal end configured to actuate a second feature of the spinal implant. Rotation of the first shaft in a first direction actuates the first feature and causes rotation of the second shaft in a second direction to actuate the second feature.

11 Claims, 11 Drawing Sheets

INSTRUMENT FOR INSERTION AND DEPLOYMENT OF FEATURES ON AN IMPLANT

CROSS-REFERENCE TO RELATED APPLICATIONS

The present application claims priority from U.S. Provisional Application 61/260,323 filed on Nov. 11, 2009 and entitled "Instrument for Insertion and Blade Deployment of an Implant," and is incorporated herein by reference in its entirety. The present application is related to U.S. application Ser. No. 12/852,033 filed on Aug. 6, 2010, entitled "Stand-Alone Interbody Fixation System," which claims priority from U.S. Provisional Application 61/231,967 filed on Aug. 6, 2009, and entitled "Stand Alone Interbody Fixation System," and is incorporated herein by reference in its entirety.

FIELD

The present disclosure generally relates to the field of spinal orthopedics, and more particularly to methods and systems for surgical instruments for the spine.

BACKGROUND

The spine is a flexible column formed of a plurality of bones called vertebra. The vertebrae are hollow and piled one upon the other, forming a strong hollow column for support of the cranium and trunk. The hollow core of the spine houses and protects the nerves of the spinal cord. The different vertebrae are connected to one another by means of articular processes and intervertebral, fibrocartilaginous bodies.

The intervertebral fibro-cartilages are also known as intervertebral disks and are made of a fibrous ring filled with pulpy material. The disks function as spinal shock absorbers and also cooperate with synovial joints to facilitate movement and maintain flexibility of the spine. When one or more disks degenerate through accident or disease, nerves passing near the affected area may be compressed and are consequently irritated. The result may be chronic and/or debilitating back pain. Various methods and apparatus have been designed to relieve such back pain, including spinal fusion using an interbody spacer or suitable graft using techniques such as Anterior Lumbar Interbody Fusion (ALIF), Posterior Lumbar Interbody Fusion (PLIF), or Transforaminal Lumbar Interbody Fusion (TLIF) surgical techniques. The implants used in-these techniques, also commonly referred to as vertebral body replacements (VBR) devices, are placed in the interdiscal space between adjacent vertebrae of the spine. Many times an exterior plate is used in conjunction with the VBR to hold the adjacent vertebrae while the fusion occurs.

SUMMARY

A surgical instrument for inserting an implant includes a first shaft having an axial bore and including a distal end configured to actuate a first feature of a spinal implant and a second shaft extending through the axial bore of the first shaft and including a distal end configured to actuate a second feature of the spinal implant. The first shaft rotates in a first direction to actuate the first feature and the second shaft rotates in a second direction to actuate the second feature. In other features, the first direction is opposite from the second direction.

In other features, the surgical instrument further comprises a gear system that transfers torque from the first shaft to the second shaft when the first shaft is rotated causing the second shaft to rotate in the opposite direction. A drive gear rotates with the first shaft and a follower gear rotates with the second shaft, wherein a transfer gear transfers torque from the drive gear to the follower gear.

In other features, the surgical instrument further includes a coupling member configured to couple with the spinal implant and that includes an axial bore, wherein the first shaft extends through the axial bore of the coupling member. In still other features, the surgical instrument further includes a sleeve having a channel configured to slide relative to the coupling member to attach the implant to the coupling member.

In other features, the surgical instrument further includes a positioning locator at a distal end of the coupling member, wherein the positioning locator is visible under fluoroscopy to locate an edge of the implant. In still other features, the surgical instrument further includes a guide pin in the channel configured to slide in a track on the coupling member. In still other features, the distal end of the first shaft and the distal end of the second shaft includes at least one of a splined projection and a hexagonal projection. In still other features, the surgical instrument further includes an anti-rotation pin that limits the rotation of at least one of the first shaft and the second shaft.

A system for inserting a spinal implant and actuating features of the implant includes an implant including a first deployment feature and a second deployment feature configured to engage with vertebrae, and an instrument including, a first shaft with an axial bore and a first engagement feature at a distal end, a second shaft extending through the axial bore with a second engagement feature at a distal end, and a coupling member that couples the implant to the first shaft and the second shaft. The first engagement feature actuates the first deployment feature and the second engagement feature actuates the second deployment feature.

In other features, the first engagement feature and the second engagement feature includes at least one of a splined projection and a hexagonal projection. The instrument rotates the first deployment feature in a first direction and the second deployment feature in a second direction. The first direction is opposite from the second direction. In still other features, the instrument further includes a sleeve that slides relative to the coupling member to couple the implant to an end of the coupling member.

A method of inserting a spinal implant and actuating features of the implant includes coupling a spinal implant to an instrument that includes a first shaft and a second shaft, positioning the spinal implant in a surgical area, and applying a force to rotate the first shaft and to actuate a first deployment feature of the spinal implant that engages with a vertebra in the surgical area. A gear set transfers a portion of the force to rotate the second shaft and to actuate a second deployment feature of the spinal implant that engages with an adjacent vertebra in the surgical area.

In other features, the method further includes positioning the second shaft in an axial bore of the first shaft. The method further includes coupling the spinal implant to the instrument includes sliding a sleeve relative to a coupling member that engages with the spinal implant. The method further includes limiting rotation of the first shaft to prevent actuation of at least one of the first feature and the second feature beyond a predetermined angle. The method further includes decoupling the spinal implant from the instrument, wherein the first and second deployment features remain engaged with the vertebrae in the surgical area.

DETAILED DESCRIPTION

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

Implants or vertebral body replacements may be placed in the interdiscal space between adjacent vertebrae of the spine. The implants may include one or more features that are deployed to affix the implants to the adjacent vertebrae. For example, a stand-alone interbody fixation system, as disclosed in U.S. application Ser. No. 12/852,033 filed on Aug. 6, 2010, entitled "Stand-Alone Interbody Fixation System," and incorporated herein by reference, provides a solid fixation in all aspects by using counter-rotating blades that provide fixation to the vertebrae. Such implants may be inserted, positioned, and deployed by various embodiments of the instrument of the present disclosure. As can be understood by one skilled in the art, these embodiments are shown for illustrative purposes and are not intended to limit the scope of the invention.

The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

Figure 1:
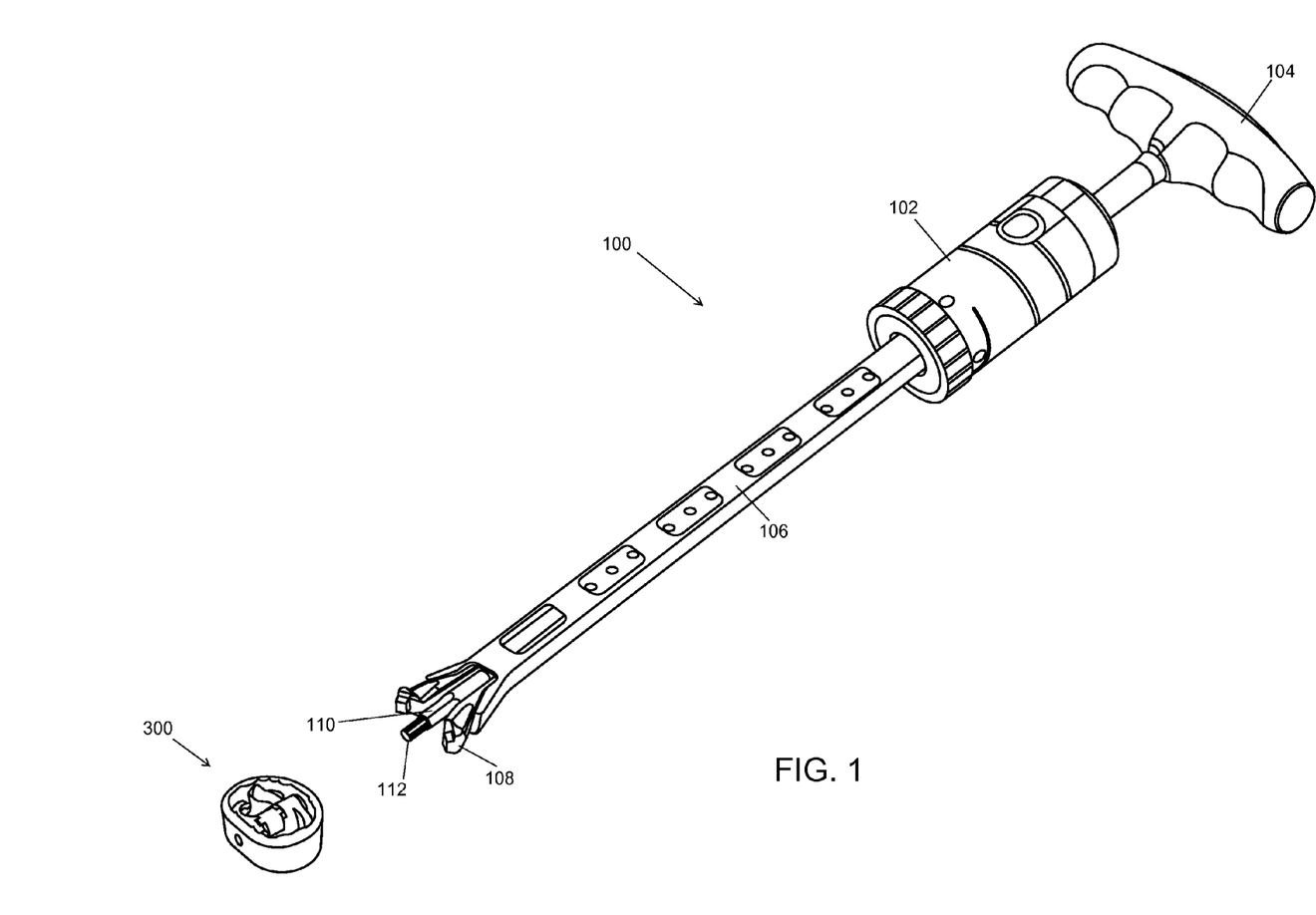
FIG. 1 is a perspective view of a surgical instrument according to the principles of the present disclosure and an implant.
Figure 2:
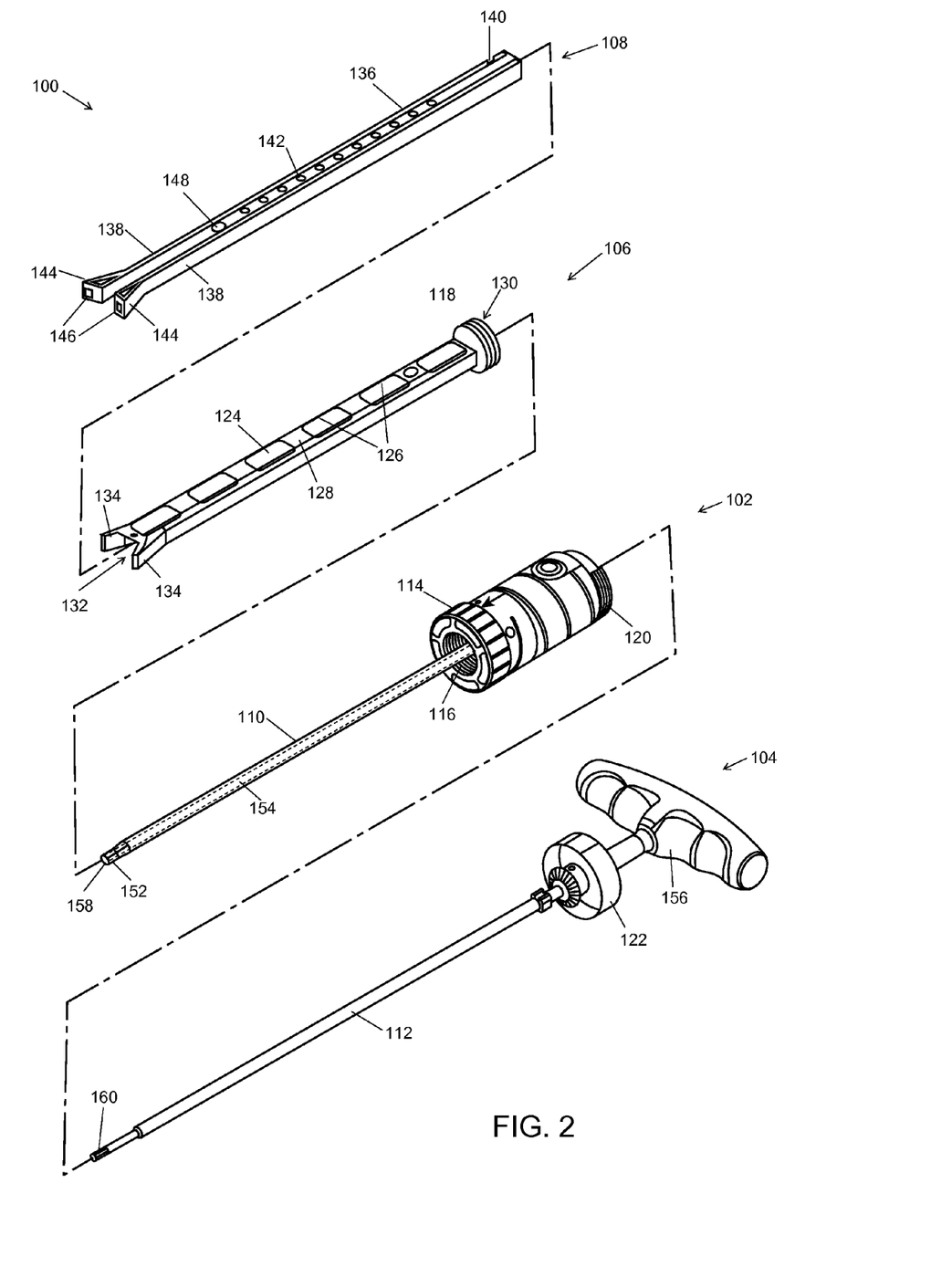
FIG. 2 is a partially exploded perspective view of the surgical instrument according to the principles of the present disclosure.

Referring to FIGS. 1 and 2, a surgical instrument 100 according to the principles of the present disclosure is shown. The instrument 100 includes features to enable insertion of an implant 300 into the spinal area of a patient and to enable actuation of additional features of the implant 300 after insertion. The instrument includes a housing 102, a handle assembly 104, a sleeve 106, a clamping member 108, an outer shaft 110, and an inner shaft 112. The clamping member 108 includes features that enable coupling of the instrument 100 with the implant 300. The sleeve 106 includes features that actuate the coupling member 108 to couple the implant 300. When the implant 300 is coupled, the instrument 100 may be used to position the implant 300 in the spinal area of the patient. The outer shaft 110 and the inner shaft 112 include features that actuate the additional features of the implant 300. For example, once the implant 300 has been positioned in the spinal area, the outer shaft 110 and the inner shaft 112 may be rotated to deploy features of the implant 300 that engage with vertebrae in the spinal area.

Referring now to FIG. 2, a partial exploded view shows additional features of the instrument 100. The housing 102 includes features for attachment of the sleeve 106, the clamping member 108, the outer shaft 110, and the handle assembly 104. The housing 102 includes a wheel 114 that freely rotates on the distal end of the housing 102 and includes features that engage with the sleeve 106. For example, the wheel 114 may include a thread 116 on an inner surface of the wheel 114 that engages with a corresponding threaded portion 118 on the proximal end of the sleeve 106. The housing 102 may include a threaded portion 120 at the proximal end for attachment of the handle assembly 104. For example, the threaded portion 120 may engage with threads of a cap 122 on the handle assembly 104.

The sleeve 106 includes a channel 124 that extends the length of the sleeve 106 and is configured to receive the clamping member 108. The channel 124 may be formed by boring a first series of windows 126 on a first side of the sleeve. The windows 126 may be cut into the sleeve 106 until a wall of material remains on a second side of the sleeve opposite the first side. After the first series of windows 126 has been cut, a second series of windows may be cut through the second side of the sleeve until cross members 128 of material remain on the first side of the sleeve. The second series of windows may be spaced to remove remaining material between the first series of windows 126. The resulting channel 124 is configured to permit sliding engagement with the clamping member 108.

The sleeve 106 forms an opening 130 at the proximal end to permit passage of the clamping member 108 through the channel 124 into the housing 102. The sleeve 106 forms a mouth 132 at the distal end that allows for sliding engagement with the clamping member 108. The mouth 132 may include flared portions 134 that flare away from a center line of the instrument 100. The flared portions 134 are configured to engage with the clamping member 108 and to couple the implant 300 to the instrument 100 as described below.

Figure 8:
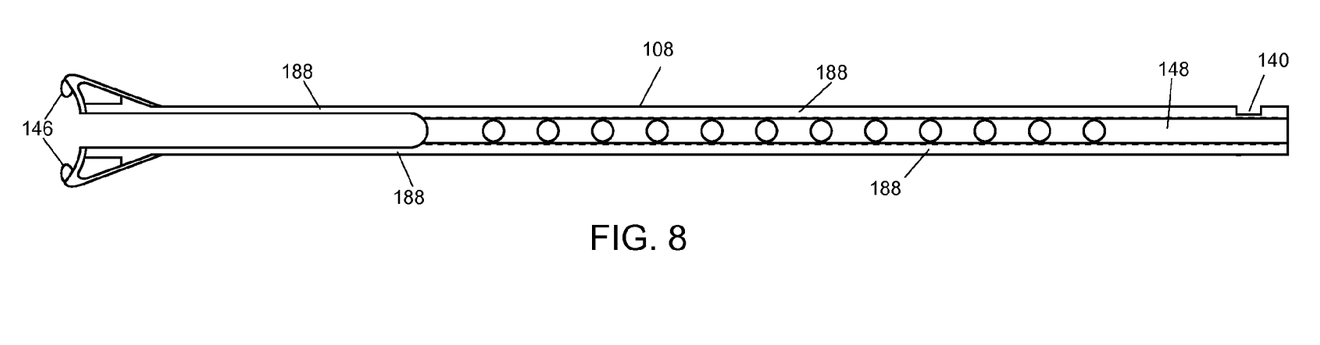
FIG. 8 is a top elevational view of a clamping member of the surgical instrument according to the principles of the present disclosure.
Figure 9:
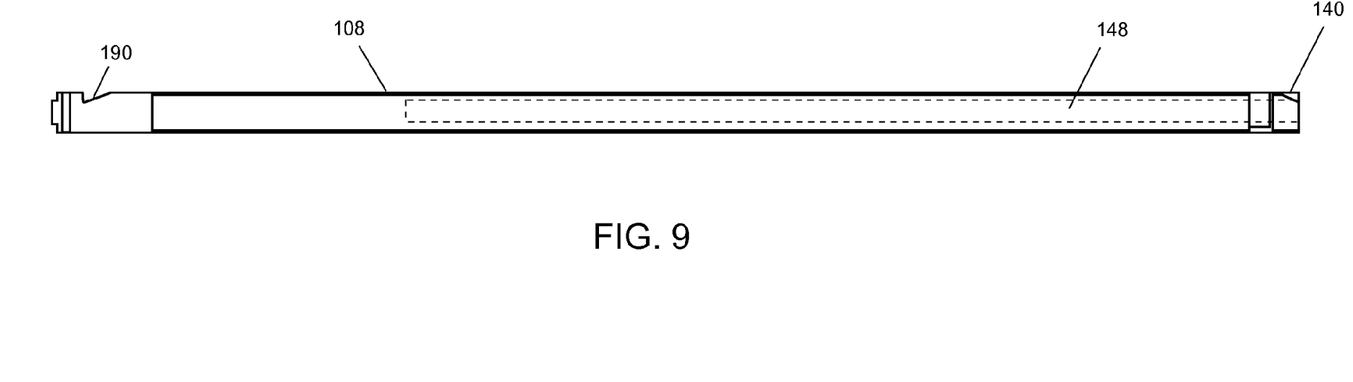
FIG. 9 is a side elevational view of the clamping member of the surgical instrument according to the principles of the present disclosure.

Continuing with FIG. 2, the clamping member 108 includes an elongated portion 136 and a pair of arms 138. The elongated portion 136 extends through the channel 124 to engage with the housing 102. At the proximal end of the elongated portion 136, a locking feature 140 is configured to fixedly attach the clamping member 108 to the housing 102. For example the locking feature 140 may include a notch cut into the clamping member 108 that engages with a lock pin (not shown) inside the housing 102. The elongated portion 136 may further include one or more holes 142 to facilitate cleaning of the instrument 100 and to reduce the weight. The pair of arms 138 extends from the distal end of the elongated portion 136 and terminates in a pair of tips 144. The tips 144 may flare away from the center line of the instrument 100 similar to the flared portions 134 of the sleeve 106. The tips 144 may include projections 146 that partially extend towards the center line of the instrument 100. In other features, the projections 146 may partially extend towards the distal end of the instrument 100. The clamping member 108 further includes a first axial bore 148 that extends the length of the elongated portion 136 to enable the outer shaft 110 to pass through the clamping member 108 as depicted in FIGS. 8 and 9.

Figure 10:
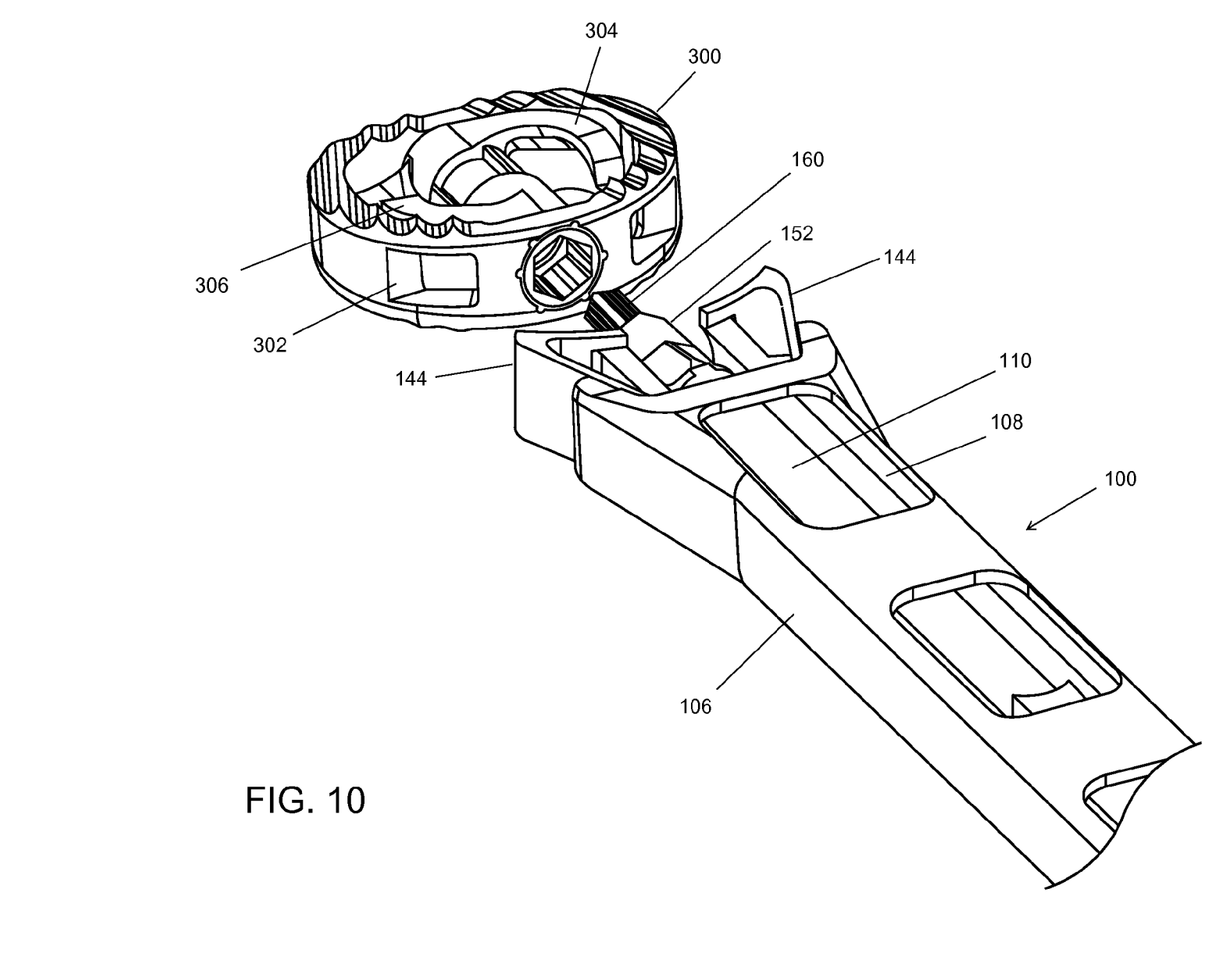
FIGS. 10-12 are partial perspective views of a distal end of the surgical instrument according to the principles of the present disclosure and an implant.

Once the sleeve 106 and clamping member 108 are coupled within the housing 102 and the wheel 114 on the housing is rotated, the threaded portion 118 of the sleeve 106 advances along the thread 116 of the wheel 114 causing the sleeve 106 to slide relative to the clamping member 108. For example, rotating the wheel 114 in a first direction advances the sleeve 106 towards the distal end of the instrument 100 while rotating the wheel in a second direction retracts the sleeve 106 towards the proximal end of the instrument 100. As the sleeve 106 advances towards the distal end of the instrument 100, the flared portions 134 engage with the tips 144. The flared portions 134 compress the tips 144 towards the center line of the instrument 100 causing the arms 138 to flex inwardly towards the center line. As shown in FIG. 10, the tips 144 are configured to engage with corresponding holes 302 on the implant 300. As the tips 144 are compressed, the projections 146 provide a clamping force on the implant 300 to couple the implant 300 to the instrument 100.

Figure 3:
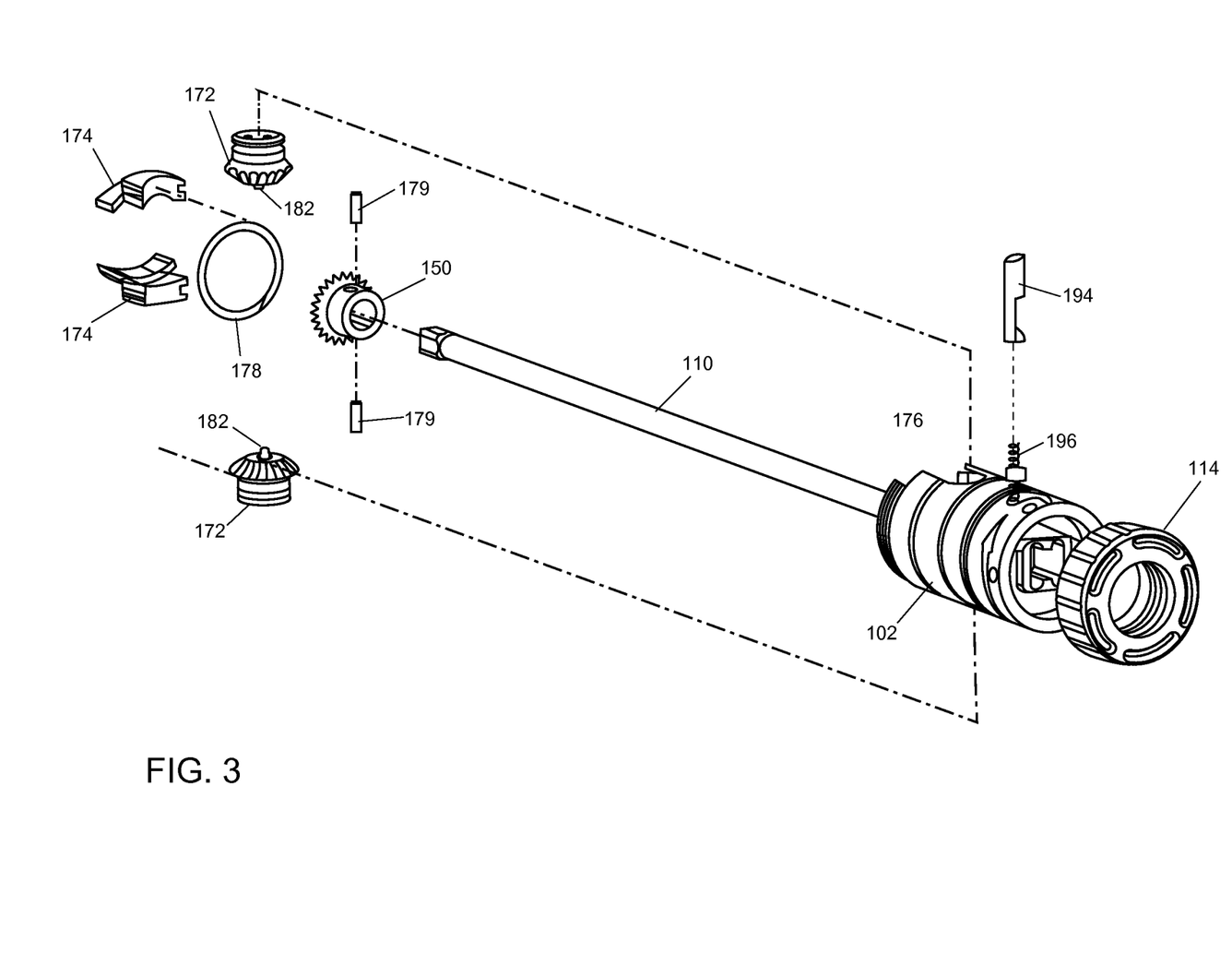
FIG. 3 is an exploded perspective view of a housing and a first shaft of the surgical instrument according to the principles of the present disclosure.
Figure 11:
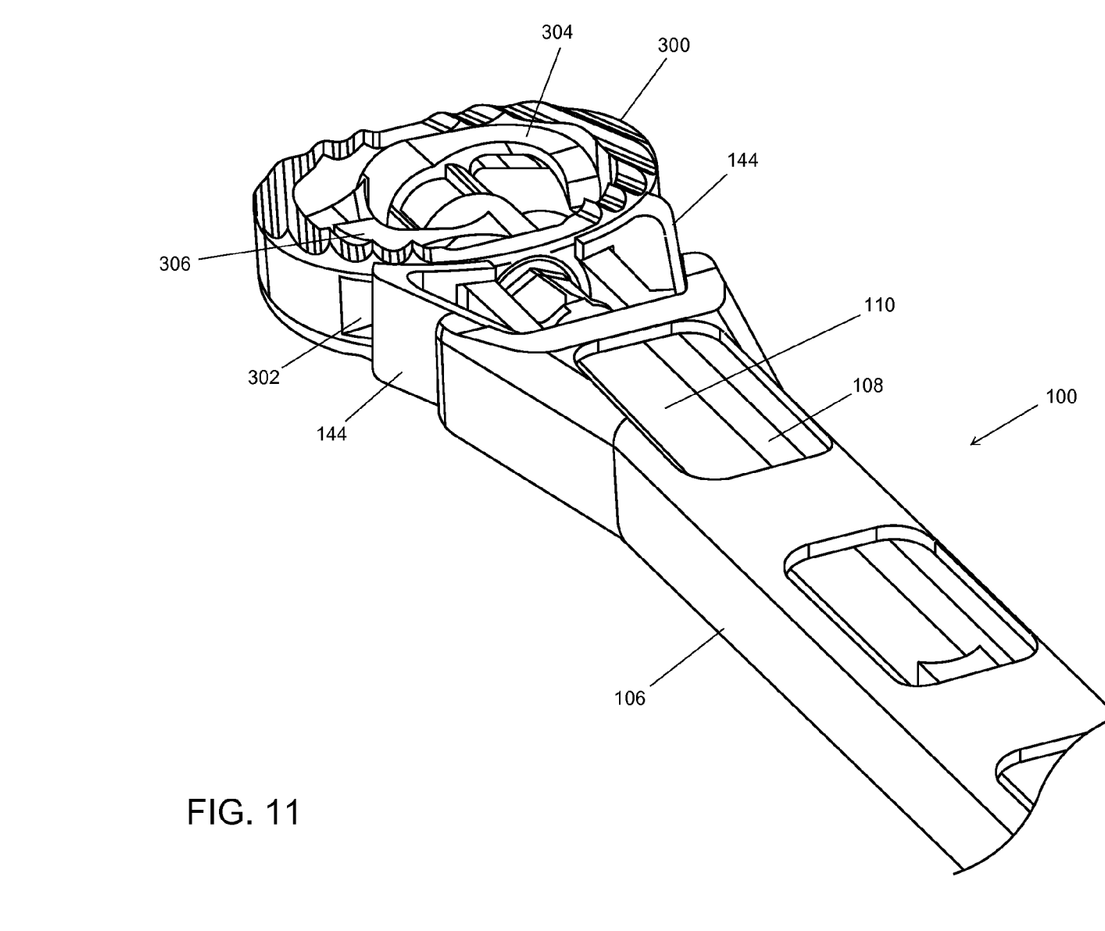
Figure 12:
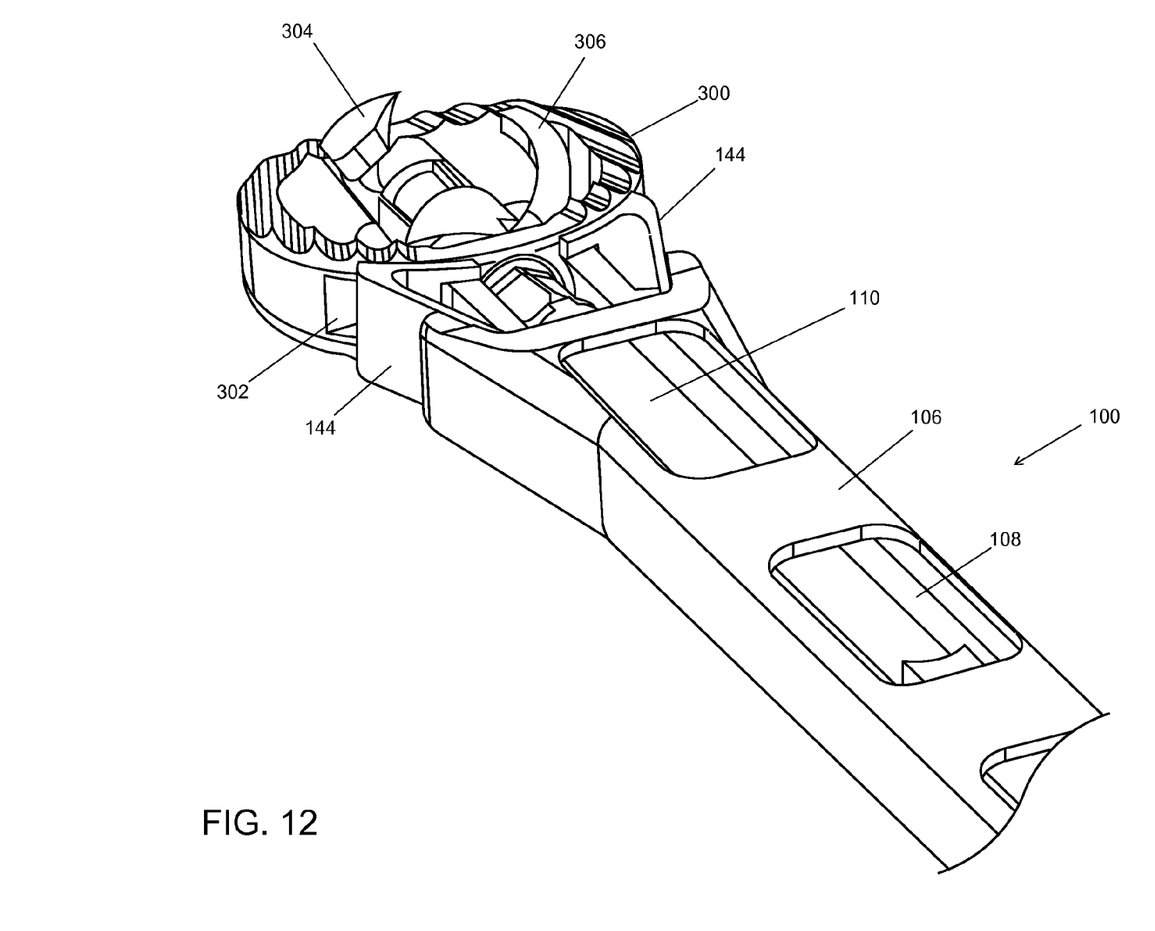

Continuing with FIG. 2, the outer shaft 110 extends from the housing 102 through the first axial bore 148 in the clamping member 108. The outer shaft 110 may freely rotate in the first axial bore 148 relative to the clamping member 108. Referring to FIGS. 2 and 3, the proximal end of the outer shaft 110 may couple with a follower gear 150 inside the housing 102 and the distal end extends through the axial bore 148 and past the mouth 132 of the sleeve 106. The distal end of the outer shaft 110 includes a first engagement feature 152 configured to actuate a first deployment feature 304 of the implant 300 as depicted in FIGS. 10-12. For example, the first engagement feature 152 may include a hexagonal projection. The outer shaft 110 further includes a second axial bore 154 extending through the length of the outer shaft 110 from the proximal end to the distal end.

Figure 4:
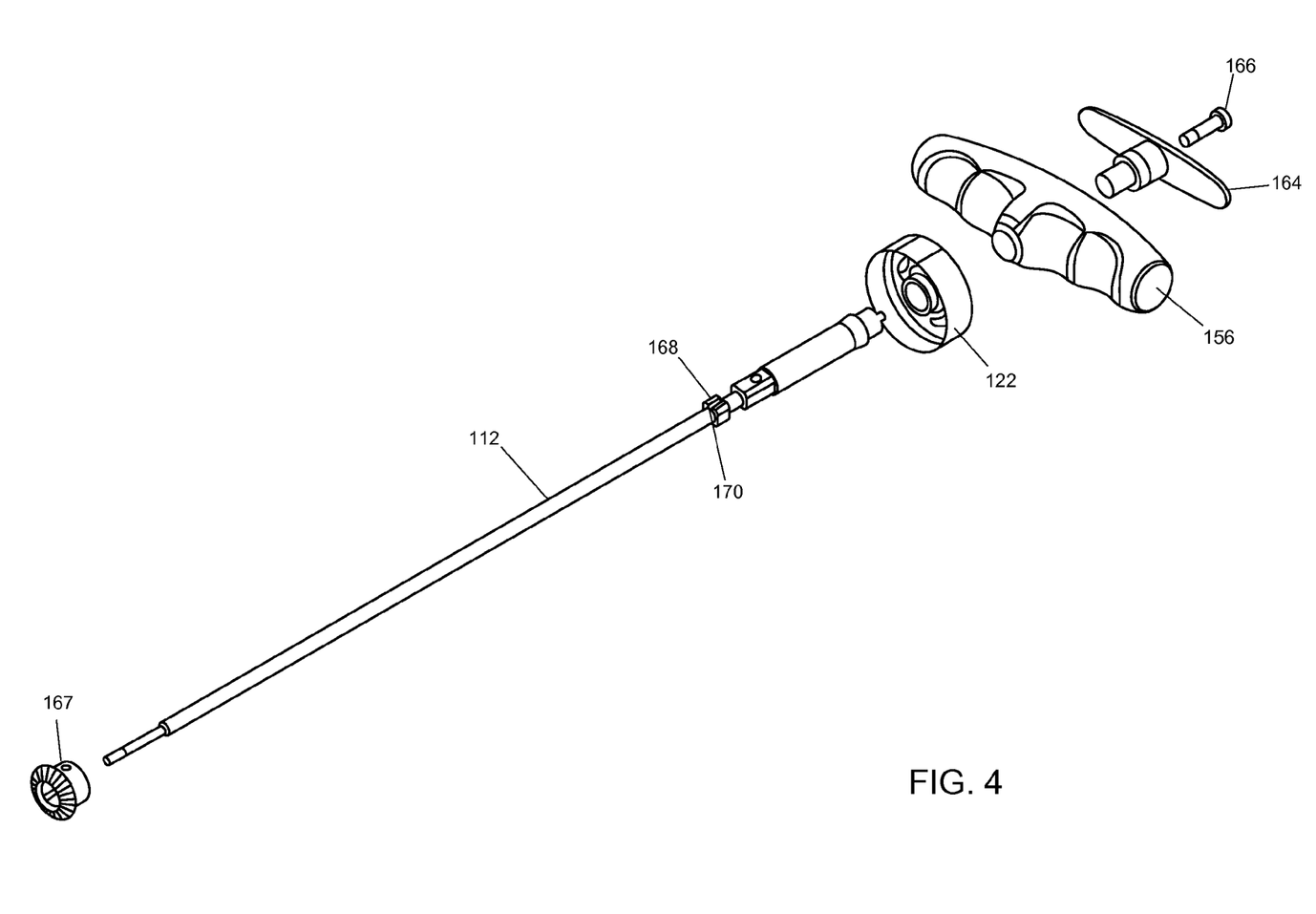
FIG. 4 is an exploded perspective view of a handle assembly and a second shaft of the surgical instrument according to the principles of the present disclosure.

Referring now to FIGS. 2 and 4, the inner shaft 112 extends from the handle assembly 104 through the second axial bore 154 in the outer shaft. The inner shaft 112 freely rotates in the second axial bore 154 relative to the outer shaft 110. The proximal end of the inner shaft 112 may couple with a handle 156 and a distal end may extend past an opening 158 in the first axial bore 148. The distal end of the inner shaft 112 includes a second engagement feature 160 configured to actuate a second deployment feature 306 of the implant as depicted in FIGS. 10-12. For example, the second engagement feature 160 may include a splined projection.

Referring now to FIGS. 3 and 4, exploded views of the handle assembly 104, inner shaft 112, housing 102, and outer shaft 110 are shown in greater detail. The handle assembly 104 includes the cap 122, the handle 156, and a striking member 164. The inner shaft 112 may pass though the cap 122 and the handle 156 to connect with the striking member 164 using a screw 166 or other fixation member. The cap 122 couples the handle assembly 104 to the housing 102 and allows rotation of the handle 156 and inner shaft 112. When the operator applies torque to rotate the handle 156, the inner shaft 112 rotates together and in the same direction as the handle 156. In addition, the operator may apply a striking force to the striking member 164 to drive the implant 300 further into the spinal area. The striking member 164 transfers the striking force to the inner shaft 112.

A drive gear 167 and an alignment block 168 are disposed along the proximal end of the inner shaft 112. The drive gear 167 may be fixedly attached to the inner shaft 112 to rotate with the inner shaft 112. The alignment block 168 may be fixedly attached to or formed on the inner shaft 112 and positioned to align the inner shaft 112 and the outer shaft 110 during assembly of the instrument 100. The alignment block 168 may include notches 170 to align the inner shaft 112 relative to the outer shaft 110 as described below. In addition, when the operator applies a striking force to the striking member 164, the alignment block 168 may transfer the striking force to the follower gear 150 and the housing 102 rather than to the distal end of the inner shaft 112. The housing 102 then transfers the striking force to the sleeve 106 to position the implant 300 deeper into the spinal area. This may prevent damage to the engagement features of the shafts.

Figure 5:
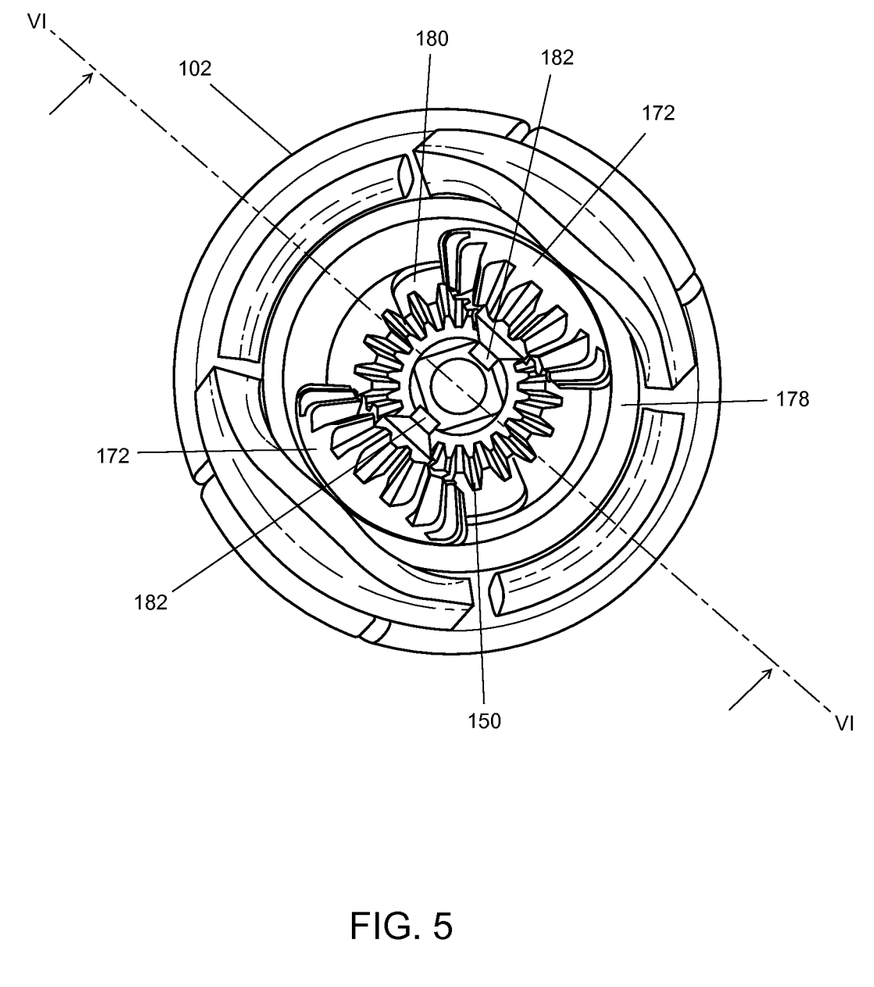
FIG. 5 is a top elevational view of the housing of the surgical instrument according to the principles of the present disclosure.
Figure 6:
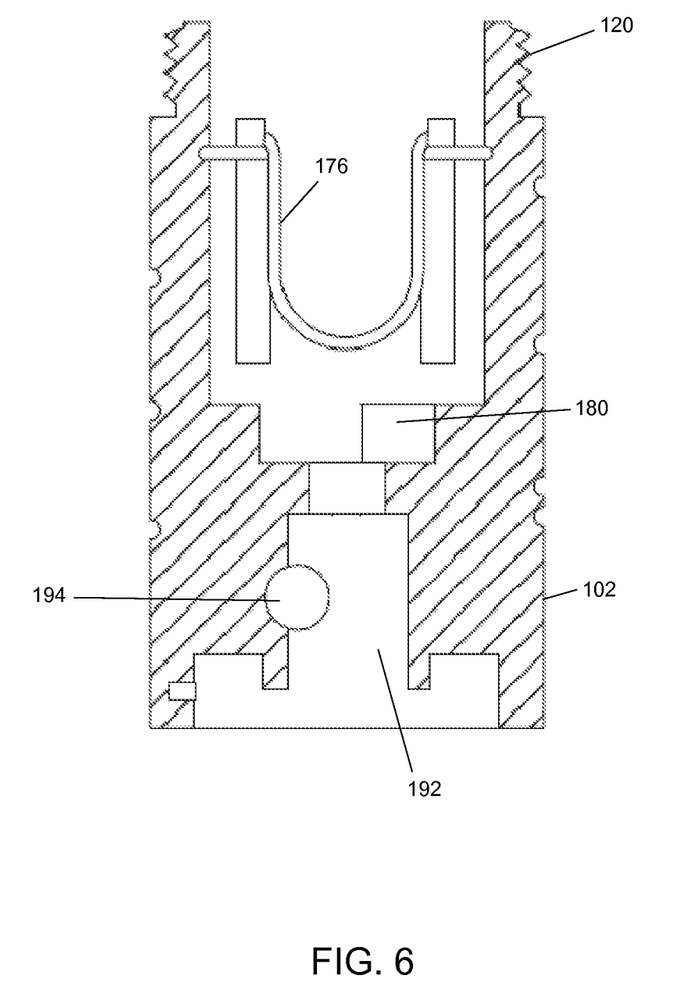
FIG. 6 is a cross-sectional view of the housing of FIG. 5 according to the principles of the present disclosure.

As depicted in FIGS. 3 and 5, the housing 102 includes a gear set that transfers torque from the drive gear 167 to the outer shaft 110. The gear set includes one or more transfer gears 172 configured to be driven by the drive gear 167 on the inner shaft 112. The transfer gears 172 may be, for example, beveled gears. Referring now to FIGS. 3 and 6, the transfer gears 172 may be rotatably fixed in removable sleeves 174 disposed in U-shaped channels 176 of the housing 102. A clip 178 may lock the sleeves 174 into the U-shaped channels 176.

When the operator applies torque to the handle 156, the drive gear 167 rotates in the same direction as the handle 156. The inner shaft 112, also attached to the handle 156, rotates in the same direction. The drive gear 167 causes the transfer gears 172 to rotate and transfer torque to the follower gear 150 attached to the proximal end of the outer shaft 110. The transfer gears 172 cause the follower gear 150 to rotate in the opposite direction as the drive gear 167. Thus, the outer shaft 110, which is attached to the follower gear 150, rotates in the opposite direction as the inner shaft 112. Thus, when the operator rotates the handle 156 in one direction, the inner shaft 112 and the outer shaft 110 counter-rotate.

One or more anti-rotation pins 179 may be used attach the follower gear 150 and to prevent the inner shaft 112 and the outer shaft 110 from rotating beyond a predetermined angle. For example, the anti-rotation pins 179 may radially extend away from the center line of the instrument 100 in a cavity 180 of the housing 102. The cavity 180 may prevent rotation of the pins 179 beyond the predetermined angle. For example, the anti-rotation pins 179 may prevent over-rotation of the first and second deployment features 304, 306 of the implant 300.

The transfer gears 172 may also include one or more alignment nibs 182 that extend from the center of the transfer gears 172 towards the inner shaft 112. The alignment nibs 182 may be used in conjunction with the notches 170 of the alignment block 168 to align the inner shaft 112 with the outer shaft 110 during assembly. For example, the inner shaft 112 may not extend through the opening 158 unless the alignment nibs 182 are lined up with the notches 170. When the alignment nibs 182 pass through the notches 170, then the first and second engagement features 152 and 160 are properly aligned for engagement with corresponding features on the implant 300.

Figure 7:
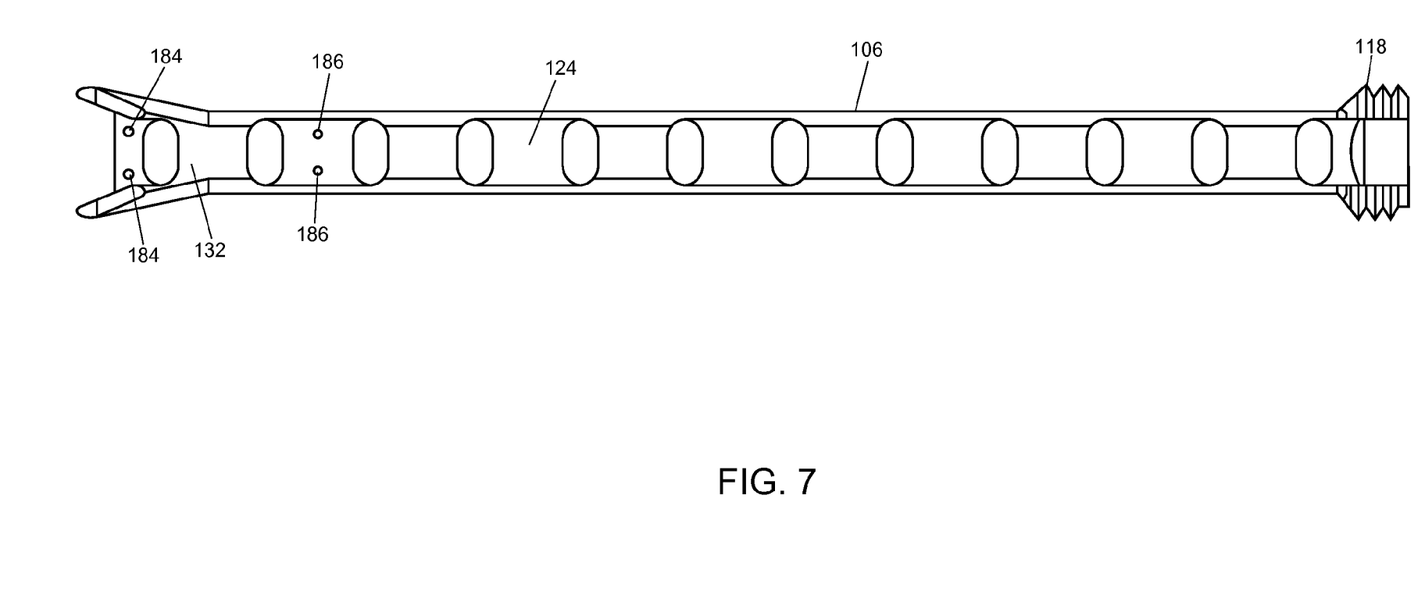
FIG. 7 is a top elevational view of a sleeve of the surgical instrument according to the principles of the present disclosure.

Referring now to FIGS. 7-9, the sleeve 106 and clamping member 108 are shown in greater detail. The sleeve 106 may include a first set of guide pins 184 on an inner surface of the mouth 132. The sleeve 106 may include a second set of guide pins 186 on an inner surface of the channel 124. The guide pins 184, 186 slidably engage with a track 188 on the clamping member 108. The guide pins 184, 186 prevent overdeflection of the arms 138 when the sleeve 106 advances towards the distal end of the clamping member 108. Additional guide pins may be provided at other locations inside the channel 124 to engage with the track 188 and maintain structural integrity of the clamping member 108.

The clamping member 108 may include a positioning marker 190 on the tips 144 to aid in locating the position of the implant 300 relative to the spinal area under fluoroscopy. The positioning marker 190 may be a cutout or notch in a sidewall of the tips 144. In additional features, the clamping member 108 may attach to the distal end of the housing 102 using the locking feature 140. For example, the clamping member 108 may be inserted into a receptacle 192 in the distal end of the housing 102 as seen in FIGS. 3 and 6. The locking feature 140 may then engage with a lock pin 194 disposed in the housing 102. The lock pin 194 may include a spring 196 to facilitate locking and release of the lock pin 194 from the locking feature 140.

Referring to FIGS. 10-12, the instrument 100 may be used to couple the implant 300 to the distal end of the instrument 100 and actuate features of the implant 300. In FIG. 10, the distal ends of the first shaft 110 and the second shaft 112 project from the axial bore 148 in the clamping member 108 so that the first and second engagement features 152 and 160 may engage with corresponding features of the implant 300. The sleeve 106 is retracted so that the flared portions 134 do not compress the tips 144 of the clamping member 108. Thus, the projections 146 on the tips 144 may engage with the holes 302 in the implant 300. In FIG. 11, the projections 146 are engaged with the implant 300 and the sleeve 106 may be advanced towards the distal end of the instrument 100 using the wheel 114. The coupling member 108 holds the implant 300 to the outer shaft 110 and the inner shaft 112, enabling the first and second engagement features 152 and 160 to engage with corresponding receptacles in the implant 300. In FIG. 12, the operator applies torque to rotate the handle 156 which causes the inner shaft 112 to rotate and actuate the first deployment feature 304 of the implant. The gear set coupling the inner shaft 112 and the outer shaft 110 transfers torque from the inner shaft 112 to the outer shaft 110. The outer shaft 110 thus rotates in the opposite direction to actuate the second deployment feature 306 of the implant 300.

Example embodiments of the methods and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

The invention claimed is:

1. A surgical instrument for inserting a spinal implant comprising:
    a first shaft having an axial bore and including a distal end configured to engage and actuate a first feature of the spinal implant; and
    a second shaft extending through the axial bore of the first shaft and including a distal end configured to engage and actuate a second feature of the spinal implant,
    wherein rotation of the first shaft in a first direction actuates the first feature and causes rotation of the second shaft in a second direction to actuate the second feature,
    wherein the first direction is opposite from the second direction; a drive gear that rotates with the first shaft and a follower gear that rotates with the second shaft, wherein a transfer gear transfers torque from the drive gear to the follower gear; and the distal end of the first shaft and the distal end of the second shaft each include at least one of a splined projection and a hexagonal projection.

2. The surgical instrument of claim 1, further comprising a handle coupled with the first shaft and configured to rotate the first shaft in the first direction.

3. The surgical instrument of claim 1, further comprising a coupling member configured to couple with the spinal implant and that includes an axial bore, wherein the first shaft extends through the axial bore of the coupling member.

4. The surgical instrument of claim 3, further comprising a sleeve having a channel configured to slide relative to the coupling member to attach the implant to the coupling member.

5. The surgical instrument of claim 3, further comprising a positioning locator at a distal end of the coupling member, wherein the positioning locator is visible under fluoroscopy to locate an edge of the implant.

6. The surgical instrument of claim 4, further comprising a guide pin in the channel and a track on the coupling member, wherein the guide pin slides in the track on the coupling member to guide movement of the sleeve relative to the coupling member.

7. The surgical instrument of claim 1, further comprising an anti-rotation pin that limits the rotation of at least one of the first shaft and the second shaft.

8. A surgical instrument for inserting a spinal implant comprising:
    a first shaft having a first axial bore and including a first distal end with a first engagement feature; and
    a second shaft extending through the first axial bore of the first shaft and including a second distal end with a second engagement feature,
    wherein rotation of the first shaft in a first direction causes rotation of the second shaft in a second opposite direction; a drive gear that rotates with the first shaft and a follower gear that rotates with the second shaft, wherein a transfer gear transfers torque from the drive gear to the follower gear; and the distal end of the first shaft and the distal end of the second shaft each include at least one of a splined projection and a hexagonal projection.

9. The surgical instrument of claim 8, wherein the first engagement feature engages and rotates a first deployment feature of the spinal implant to deploy the first deployment feature into a first vertebra of a pair of adjacent vertebrae.

10. The surgical instrument of claim 8, wherein the second engagement feature engages and rotates a second deployment feature of the spinal implant to deploy the second feature into a second vertebra of the pair of adjacent vertebrae.

11. A spinal instrument and implant comprising:
    an intervertebral implant including spacer, a first rotatable anchor, and a second rotatable anchor;
    a first shaft having a first axial bore and including a first distal end with a first projection that engages a first recess of the first rotatable anchor;
    a second shaft extending through the first axial bore and including a second distal end with a second projection that engages a second recess of the second rotatable anchor;
    a coupling member having a second axial bore and a pair of arms extending distally to couple with the implant, wherein the first shaft extends through the second axial bore of the coupling member;

a sleeve having a channel that receives the coupling member and that slides relative to the coupling member to position the pair of arms relative to the implant, wherein sliding the sleeve distally positions the pair of arms inwardly to couple with the implant and sliding the sleeve proximally positions the pair of arms outwardly to uncouple from the implant;

a housing that receives proximal ends of the first shaft, the second shaft, the coupling member, and the sleeve and that includes a gear system that operably connects the proximal ends of the first shaft and the second shaft; and a handle coupled with the proximal end of the first shaft and the housing, wherein the handle rotates the first shaft in a first direction to deploy the first rotatable anchor and the gear system causes rotation of the second shaft in an opposite second direction to simultaneously deploy the second rotatable anchor; a drive gear that rotates with the first shaft and a follower gear that rotates with the second shaft, wherein a transfer gear transfers torque from the drive gear to the follower gear; and the distal end of the first shaft and the distal end of the second shaft each include at least one of a splined projection and a hexagonal projection.

* * * * *